(12) United States Patent
Chen et al.

(10) Patent No.: US 11,660,029 B2
(45) Date of Patent: May 30, 2023

(54) ELECTROCHEMICAL ELECTRODE, CONTINUOUS GLUCOSE MONITORING SENSOR AND PREPARATION METHOD THEREFOR

(71) Applicants: VivaChek Biotech (Hangzhou) Co., Ltd, Zhejiang (CN); Zhejiang University City College, Zhejiang (CN)

(72) Inventors: Yuquan Chen, Zhejiang (CN); Wei Chen, Zhejiang (CN)

(73) Assignees: VIVACHEK BIOTECH (HANGZHOU) CO., LTD, Hangzhou (CN); ZHEJIANG UNIVERSITY CITY COLLEGE, Hangzhou (CN)

( * ) Notice: Subject to any disclaimer, the term of this patent is extended or adjusted under 35 U.S.C. 154(b) by 1115 days.

(21) Appl. No.: 16/302,664

(22) PCT Filed: May 12, 2017

(86) PCT No.: PCT/CN2017/084149
§ 371 (c)(1),
(2) Date: Nov. 18, 2018

(87) PCT Pub. No.: WO2017/198116
PCT Pub. Date: Nov. 23, 2017

(65) Prior Publication Data
US 2019/0290170 A1    Sep. 26, 2019

(30) Foreign Application Priority Data

May 19, 2016   (CN) .......................... 201610339920.5
May 19, 2016   (CN) .......................... 201620464943.4

(51) Int. Cl.
*A61B 5/1473*    (2006.01)
*C23C 18/16*     (2006.01)
(Continued)

(52) U.S. Cl.
CPC .......... *A61B 5/1473* (2013.01); *A61B 5/1486* (2013.01); *A61B 5/14532* (2013.01);
(Continued)

(58) Field of Classification Search
CPC . A61B 5/1473; A61B 5/14532; A61B 5/1486; A61B 5/14865; A61B 5/1495;
(Continued)

(56) References Cited

U.S. PATENT DOCUMENTS

| | | | | |
|---|---|---|---|---|
| 5,212,018 A | * | 5/1993 | Iwamoto | G01N 27/07 204/290.14 |
| 2003/0022102 A1 | * | 1/2003 | Hiraoka | H05K 3/185 430/311 |

(Continued)

FOREIGN PATENT DOCUMENTS

| CN | 101101273 A | * | 1/2008 |
| CN | 104831261 A | * | 8/2015 |
| CN | 105232058 A | * | 1/2016 |

*Primary Examiner* — Dah-Wei D. Yuan
*Assistant Examiner* — Nga Leung V Law
(74) *Attorney, Agent, or Firm* — Nz Carr Law Office

(57) ABSTRACT

Provided in the present invention are a flexible electrochemical electrode, a subcutaneous continuous glucose monitoring sensor equipped with the electrochemical electrode, and a preparation method thereof. The electrode directly uses gold layers on both sides of a chemically plated film, respectively as a working electrode and a reference-counter electrode, so as to form an electrochemical two-electrode system. Petaloid platinum nanoparticles are electrodeposited on a surface of the configured working electrode as a catalytic layer; a carbon nanotube/Nafion mesh layer functions as an anti-interference layer, and is formed thereon with an enzyme biochemical sensitive layer by means of electrostatic adsorption, after crosslinking and curing in glutaraldehyde, polyurethane mass transfer is coated to limit a protection layer, so as to prepare a flexible (Continued)

continuous glucose monitoring sensor. The sensor does not require photolithography, screen printing or other technologies to construct an electrochemical electrode system. The present invention effectively simplifies the processing technology, can easily achieve large-scale production and reduce production costs; and meanwhile, the present invention has characteristics such as a wide linear range, low detection limit, powerful anti-interference capacity, high response sensitivity and long-term stability.

5 Claims, 8 Drawing Sheets

(51) Int. Cl.
| | |
|---|---|
| C23C 18/30 | (2006.01) |
| C23C 18/20 | (2006.01) |
| C23C 18/44 | (2006.01) |
| A61B 5/145 | (2006.01) |
| A61B 5/1486 | (2006.01) |
| C23C 28/02 | (2006.01) |
| C25D 3/50 | (2006.01) |
| A61B 5/1495 | (2006.01) |
| A61B 5/00 | (2006.01) |
| B05D 5/12 | (2006.01) |

(52) U.S. Cl.
CPC ...... *A61B 5/14865* (2013.01); *C23C 18/1641* (2013.01); *C23C 18/1653* (2013.01); *C23C 18/30* (2013.01); *C23C 28/023* (2013.01); *C25D 3/50* (2013.01); *A61B 5/1495* (2013.01); *A61B 5/6847* (2013.01); *B05D 5/12* (2013.01); *C23C 18/2086* (2013.01); *C23C 18/44* (2013.01)

(58) Field of Classification Search
CPC ..... A61B 5/6847; A61B 5/685; A61B 5/6848; C23C 18/1641; C23C 18/1653; C23C 18/30; C23C 28/023; C23C 18/2086; C23C 18/44; C23C 18/1692; C23C 18/42; C23C 28/00; C23C 28/322; C23C 28/34; C25D 3/50; C25D 3/567; C25D 7/0614; B05D 5/12
See application file for complete search history.

(56) References Cited

U.S. PATENT DOCUMENTS

| | | | |
|---|---|---|---|
| 2009/0000947 A1* | 1/2009 | Akahori | C12Q 1/001 204/403.14 |
| 2013/0104740 A1* | 5/2013 | Perkins, II | B01D 67/0069 96/11 |
| 2014/0110693 A1* | 4/2014 | Zhou | H01L 51/56 438/46 |
| 2020/0258651 A1* | 8/2020 | Yamashita | H01B 7/00 |

* cited by examiner

ELECTROCHEMICAL ELECTRODE, CONTINUOUS GLUCOSE MONITORING SENSOR AND PREPARATION METHOD THEREFOR

CROSS REFERENCE TO RELATED APPLICATIONS

This application is a 35 U.S.C. § 371 national phase application of PCT/CN2017/084149, filed May 12, 2017, which application claims priority from Chinese Patent Application No. 201620464943.4, filed on May 19, 2016, and Chinese Patent Application No. 201610339920.5, filed on May 19, 2016. The entire application, including all tables, diagrams and claims is incorporated hereby as reference of the present invention.

FIELD OF THE INVENTION

The present invention relates to a biosensor, in particular to an electrochemical electrode, a continuous glucose monitoring sensor equipped with the electrochemical electrode, and a preparation method thereof. It belongs to the technical field of current measuring continuous glucose monitoring sensors.

BACKGROUND OF THE INVENTION

Diabetes is one of the common chronic diseases that poses a serious threat to human health. The disease is still incurable, but effective glycemic management can significantly reduce the incidence of complications and improve the quality of life of patients. Blood glucose detection is the gold standard for diagnosis and management of diabetes. In order to solve the inconvenience and pain caused by fingertip puncture for blood collection for many times a day, technicians skilled in the art have created a continuous glucose monitoring system (CGMS) that can be implanted subcutaneously. For example, the patent with the international application number PCT/US2005/032102 and international publication number WO/2006/029293 discloses a blood contact sensor comprising a sensor for monitoring the presence of a sample, and its assembly tool, the assembly tool having a sensor terminal fixed at the sensor. It is suitable for the combined use with the venous flow devices when assembling tools.

In order to improve the compatibility and stability of the glucose sensor in the continuous blood glucose monitoring system with the foregoing "blood contact sensor" as an example, Chinese patent CN101530327A discloses a needle current measuring type glucose sensor for real-time monitoring of subcutaneous tissues and the production method thereof. It comprises a needle-shaped reference electrode and at least one needle-shaped working electrode. The working electrode comprises a conductive layer, a polymer material inner film layer, an enzyme film layer, and a polymer material diffusion-control layer from inside out. Although the sensor can be implanted into the subcutaneous tissues through the needle electrode directly, it will produce great trauma when implanted subcutaneously as the device comprises a needle-shaped reference electrode and at least one needle-shaped working electrode. In addition, the conductive layer of the device is composed of a metal matrix, a metal transition layer and a precious metal layer from the inside out. Since the metal transition layer and the precious metal layer need to be attached to the surface of the metal matrix, the manufacturing cost is high and the processing technology is complicated.

In the prior art, the sensor also has a flexible polymer film as a substrate, on which a carbon electrode or a gold electrode is deposited, and an electrochemical three-electrode detection system is formed by layer-by-layer assembly or planar misalignment of the electrode; or achieved directly by very fine metal wire. However, most of these methods have complicated process and low scale, which makes high production cost of such products and restricts the promotion and application of the CGMS system. Moreover, for the sensor preparation process using a flexible polymer film as a substrate, depositing wires and electrodes on the insulating polymer film is usually realized by vacuum magnetron sputtering, photolithography, screen printing, jet printing, etc., but the metal layer of vacuum evaporation often has poor adhesion with the substrate, which is very easy to fall off. In the electroless plating methods of photolithography process and the film surface, dangerous or toxic reagents are usually used. With strict control on these reagents in the ROHS and WEEE standards, the surface etching process of strong oxidant required in this type of process is gradually changed to low temperature plasma surface treatment and transition layer process, but there are still some problems such as complicated processes, special requirements on the size and shape of the workpiece, and poor bonding degree between the coating and the substrate, etc. The screen printing material process is a conventional and mature technology, but there are some problems such as low precision, not easy to miniaturize, and serious material waste. Now it has gradually developed into jet printing and manufacturing, but this emerging method still faces many challenges, such as control of the characteristics of ink for jet printing, nozzle clogging, and the bonding force of substrate and ink, and curing method of the ink, etc. In addition, for the processes with extremely fine metal wires as electrodes, it is generally implemented by using expensive platinum iridium filaments having a PTFE insulating jacket. Using the wire portion without the insulating layer as a working electrode and the portion coated with Ag/AgCl silver paste or wrapped with fine Ag wire and chlorinated as a reference electrode, a two-electrode electrochemical system is realized. The raw material of such a process usually has high cost, and since the two-electrode system can be configured only in the radial direction, the electrode sensing portion is long, and it is required to implant into the deeper parts of the skin, which is prone to cause accidental damage to the blood capillary. Moreover, this kind of sensor requires complicated manufacturing process, which is not conducive to large-scale production, resulting in high production cost.

SUMMARY OF THE INVENTION

It is an object of the present invention to design an electrochemical electrode, a continuous glucose monitoring sensor equipped with the electrochemical electrode, and a preparation method thereof. The sensor does not require patterning techniques such as photolithography or screen printing, which can simplify the processing technology, lower the production cost, reduce implant trauma, and improve the sensitivity, etc.

To achieve the above object, the present invention adopts the following technical solutions.

Technical solution 1: An electrochemical electrode, comprising an electrode matrix made of a polymer film, and two sides of the electrode matrix being coated with a first conductive layer respectively, and the two conductive layers being used as a working electrode and a reference-counter electrode respectively; the working electrode is covered by a platinum black layer, a porous carbon layer, an enzyme biochemical sensitive layer and a protective layer respectively on the outer side of the first conductive layer; the electrode matrix is provided with a through hole passing through the polyurethane protective layer on both sides, and the through hole is coated with a hydrophilic polymer layer.

In some preferred embodiments, the reference-counter electrode is covered by a platinum black layer and a protection layer from the first conductive layer to the outside.

In some preferred embodiments, the protection layer is a polyurethane protection layer.

In some preferred embodiments, the first conductive layer is a gold layer.

In some preferred embodiments, the porous carbon layer is a carbon nanotube and/or a Nafion mesh layer.

In another aspect, the present invention provides an electrochemical electrode whose electrode matrix is made of a polymer film, and both sides of the electrode matrix are deposited by a gold layer as a working electrode and a reference-counter electrode respectively; the working electrode is covered by a platinum black layer, a carbon nanotube/Nafion mesh layer, an enzyme biochemical sensitive layer, a polyurethane protection layer respectively from the gold layer to the outside; the reference-counter electrode is covered by a platinum black layer and a polyurethane protection layer respectively from the gold layer to the outside; the electrode matrix is provided with a through hole passing through the polyurethane protective layer on both sides, and the through hole is coated with a hydrophilic polymer layer.

In all foregoing embodiments, the through hole is a circular hole, a square hole or an interdigitated comb hole.

In all foregoing embodiments, the thickness of the polymer film is 20 µm to 200 µm; the thickness of the conductive layer or the gold layer on both sides of the electrode matrix is at least 5 µm.

In all foregoing embodiments, a polydopamine layer is provided below the first conductive layer of the electrode.

In all foregoing embodiments, a catalytic layer is further provided on the polydopamine layer, wherein the catalytic layer is located between the first conductive layer and the polydopamine layer.

In all foregoing embodiments, the treatment and/or formation of the various layers is carried out by surface metallization technology.

Technical solution 2: A continuous glucose monitoring sensor, comprising the electrochemical electrode and the base, and the top of the electrode is in a needle shape, and the electrode tail end is fixed to the base perpendicularly.

Preferably, the thickness of the gold layer on both sides of the electrode matrix is at least 5 µm; the thickness of the polymer film is at least 20 µm.

Preferably, the through hole is a circular hole, a square hole or an interdigitated comb hole.

Technical solution 3: a method of making a continuous glucose monitoring sensor as described in the technical solution 2, comprising the following steps:
1. Providing a film material;
2. Depositing a polydopamine layer on the surface of the film material;
3. Depositing a catalytic layer on the surface of the film material;
4. Chemically depositing a gold layer on the surface of the film material;
5. Adsorbing a carbon nanotube mesh layer on the surface of the film material.

In some preferred embodiments, the film material is subjected to decontamination, and the treatment method comprises the following steps: PI slice decontamination, cutting a polymer film material having a thickness of at least 20 µm into sheets respectively, placing them in an organic solvent, such as acetone and ethanol; and performing ultrasonic treatment in deionized water for 5 minutes and drying, then removing oil dirt on the surface.

In some preferred embodiments, the method for depositing a polydopamine layer on the surface of the film material: immersing the cleaned sheet in a dopamine hydrochloride solution (pH 8.5, 2 mg/ml), placing it on a bleaching shaker at room temperature, and after oxidizing in air for 24 hours, a layer of polydopamine is formed on the surface of the sheet, after immersed and cleaned in deionized water for 8 hours, dried in a 80° C. oven.

In some preferred embodiments, the method of depositing a catalytic layer on the surface of the film material comprises the following steps: immersing the dried sheet in a 0.1 wt % Stearyl Trimethyl Ammonium Chloride (STAC) solution for 5 s, and taking out for drying, then placing it in platinum nanosol for 30 min, adsorbing a platinum nanoparticle layer on the surface of the sheet, and taking out, gently rinsing the surface with deionized water, to remove the unimmobilized platinum nanoparticles and dry.

In some preferred embodiments, chemically depositing the gold layer on the surface of the film material comprises the following steps: placing the dried sheet into a gold plating liquid (containing 10 mM chloroauric acid and 20 mM hydrogen peroxide) for 15 minutes, and then quickly placing in a 120° C. oven for annealing for 50 min, and turning off the oven, when the temperature in the oven has dropped to room temperature, taking out the sheet, at this time, a layer of bright, compact and firm gold is deposited on the surface of the sheet.

In some preferred embodiments, the steps of electrodepositing a platinum layer on the surface of the film material: placing the cleaned gold-plated electrode on a platinum plating solution (3 wt % chloroplatinic acid, 0.25 wt % lead acetate), and setting the working potential at −2.5 V and the deposition time at 120 s by the constant-voltage method using platinum filament as a counter electrode; electrodepositing a compact platinum black layer on both sides of the electrode simultaneously, and sputtering or coating an insulating layer (8) on both sides of the sheet.

In some preferred embodiments, adsorbing a carbon nanotube mesh layer on the surface of the film material: immersing the electrode in aqueous dispersion liquid of carbon nanotube (carbon nanotube aqueous dispersion liquid: 5 wt % Nafion=1:4), setting a working voltage of 1 V and a working time of 10 s by the potentiostatic method, to form a carbon nanotube mesh layer on the outer peripheral surface of the working electrode hole.

In some preferred embodiments, the film layer can be subjected to one or more of the following treatments:

Parylene insulation treatment: Sputtering or coating a Parylene insulating layer on both sides of the sheet;

or, boring to form a working surface: Making a through hole (9) by laser on the surface of the set electrode working area to form a working area;

or, crosslinking and curing: overhanging the electrode in a container with 25% glutaraldehyde at the bottom, crosslinked in a 40° C. oven for 60 min, and storing in a refrigerator at 4° C. for 2 h to firmly bond the carbon nanotube mesh layer with the substrate;

or, electro-adsorbing $GO_X$ enzyme layer: immersing the working part of the electrode in the $GO_X$ enzyme solution (BSA: $GO_X$=1:3, concentration of 30 mg/ml), setting the working voltage at 0.3V and the working time at 2400 s by the potentiostatic method using the side of the carbon nanotube mesh layer as the working electrode and the other side as the counter electrode, then storing the electrode in a 4° C. refrigerator for 8 h, so that $GO_X$ is fully embedded in the carbon nanotube mesh layer to form the $GO_X$ enzyme layer;

or, cutting electrode: cutting the sheet into a filament-like, single-layer double-sided electrode using an ultraviolet laser cutting machine;

or, forming a polyurethane protection layer: dissolving 4 wt % of polyurethane in a mixed solution of 98 v % tetrahydrofuran and 2 v % dimethylformamide to form a polyurethane solution, slowly passing the electrode sensing portion through a steel wire ring with an inner diameter of 2 mm soaked with the polyurethane solution, to form a polyurethane protection layer on the surface of the electrode;

or, assembling an electrode: fixing the electrode tail end to the base, and the lead wire area (7) on the electrode tail end is electrically connected to the sensing component in the base.

Preferably, the method of preparing platinum nanosol in the step is as follows: dissolving 0.25 mmol of chloroplatinic acid in 91.5 ml of water, dissolving 5 mg of PVP in 5 ml of water and adding to the chloroplatinic acid solution, then dissolving 1 mmol of sodium borohydride in 10 ml of water, taking 1 ml and slowing adding to the mixed solution of PVP and chloroplatinic acid, after shaking vigorously, standing at room temperature for 24 hours.

Preferably, after the $GO_X$ enzyme layer is formed in step ⑨, the enzyme layer is fully crosslinked and cured by the crosslinking and curing method described in step ⑧, and the insufficiently immobilized enzyme is washed away with deionized water.

Preferably, after forming a polyurethane protection layer in step ⑩, the electrode after filming is dried in a drying oven for 8 hours, and then the electrode is placed in a PBS buffer for 72 hours, so that the layers of the electrode are sufficiently regulated and fused.

Compared with the prior art, the present invention has the following beneficial effects. In the present invention, the gold layers on both sides of the chemically plated film form an electrochemical two-electrode system, and after assembly layer by layer, and sequentially modifying the catalytic layer, anti-interference layer, glucose oxidation enzyme layer and mass transfer limiting layer on the electrode surface, a single-sheet double-sided electrochemical electrode is formed, without requiring the photolithography or screen printing technology. It can effectively simplify the processing technology and reduce the production cost; the continuous glucose monitoring sensor equipped with the electrochemical electrode have a linear range of glucose up to 30 mM, and a detection limit of less than 0.25 mM, with high long-term stability of signals and strong anti-interference. Its sensitivity is up to 100 $\mu A/(mmol/L \cdot cm-2)$ and its response speed is fast, so it can be used for subcutaneous continuous blood glucose monitoring, moreover, the monolithic electrode structure is also effective in reducing implant trauma.

DETAILED DESCRIPTION

In order to make the technical solution of the present invention clearer, the present invention will be described in detail below with reference to FIGS. 1 to 5. It should be understood that the specific embodiments described herein are merely illustrative of the invention and are not intended to limit the scope of the invention.

Example 1

Figure 1A:
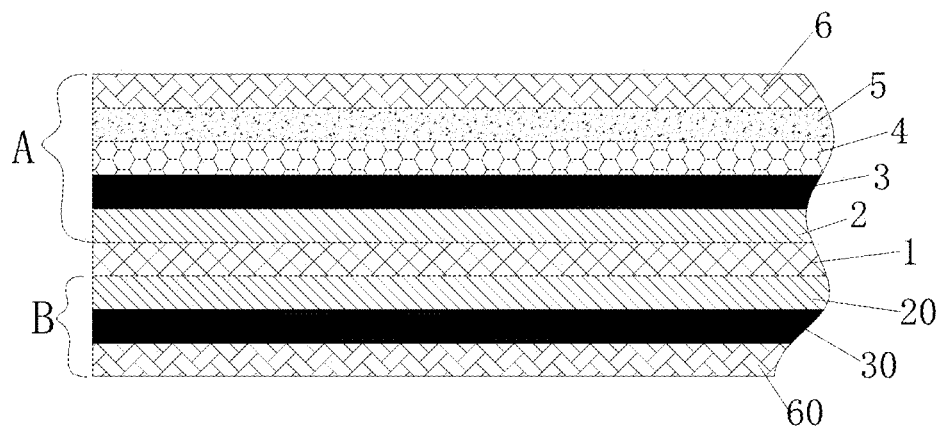
FIG. 1A is a cross-sectional structural view of an electrochemical electrode according to an embodiment of the present invention.
Figure 1B:
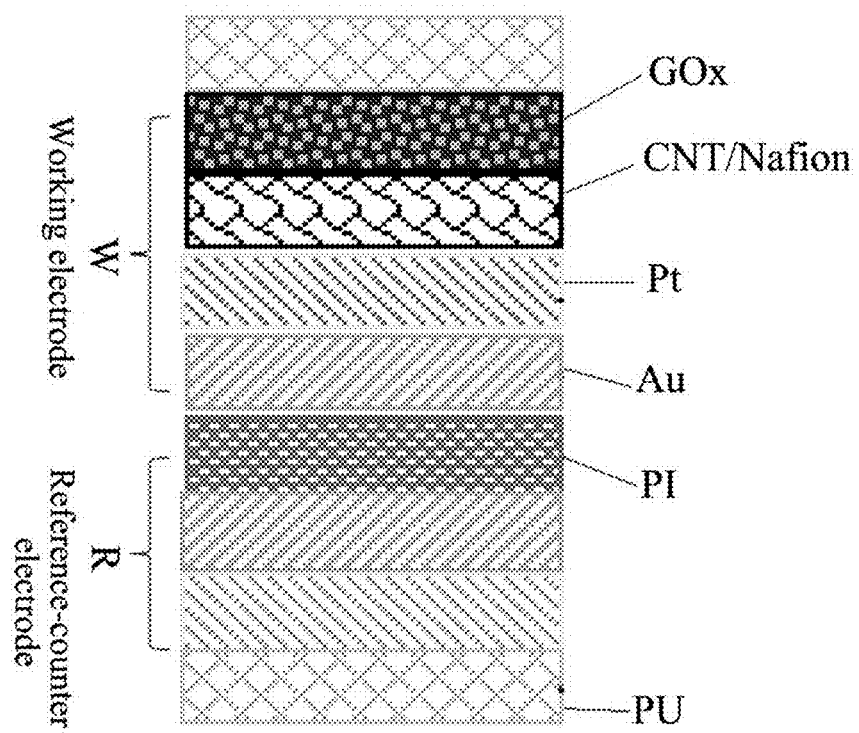
FIG. 1B is a cross-sectional structural view of an electrochemical electrode according to another embodiment of the present invention.
Figure 1C:
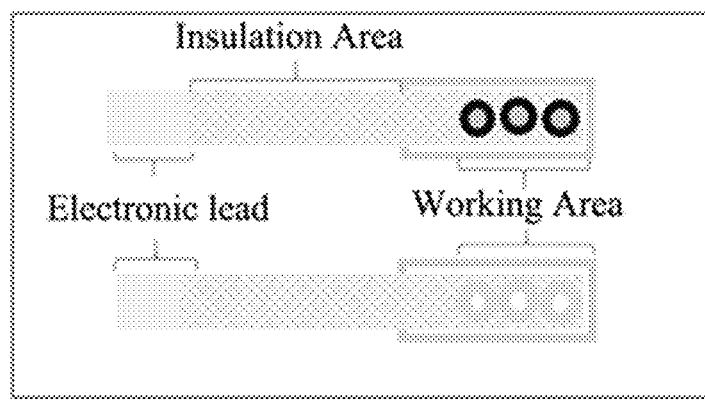
FIG. 1C is a top view of an electrochemical electrode according to another embodiment of the present invention.
Figure 1D:
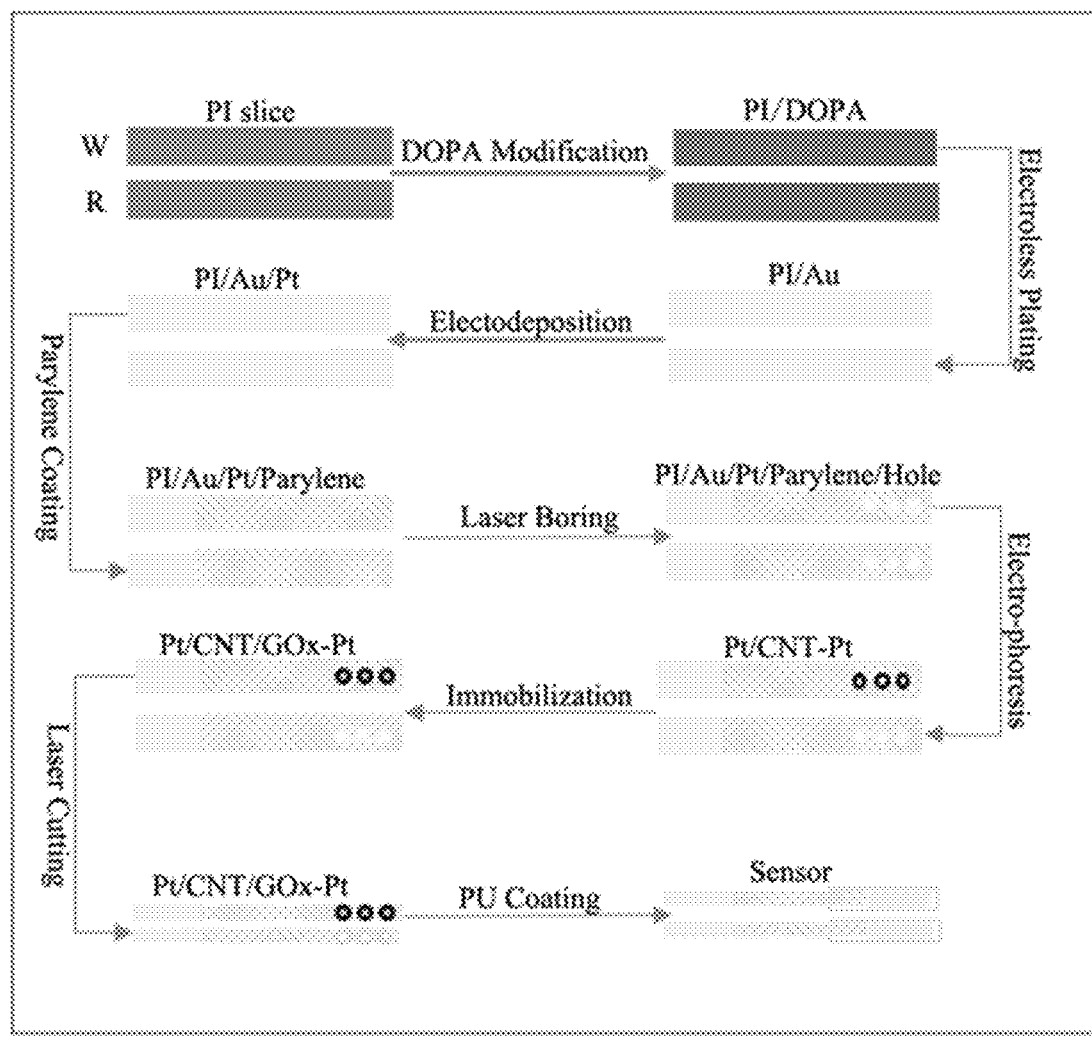
FIG. 1D is a schematic flow chart of an electrochemical electrode according to another embodiment of the present invention.
Figure 2:
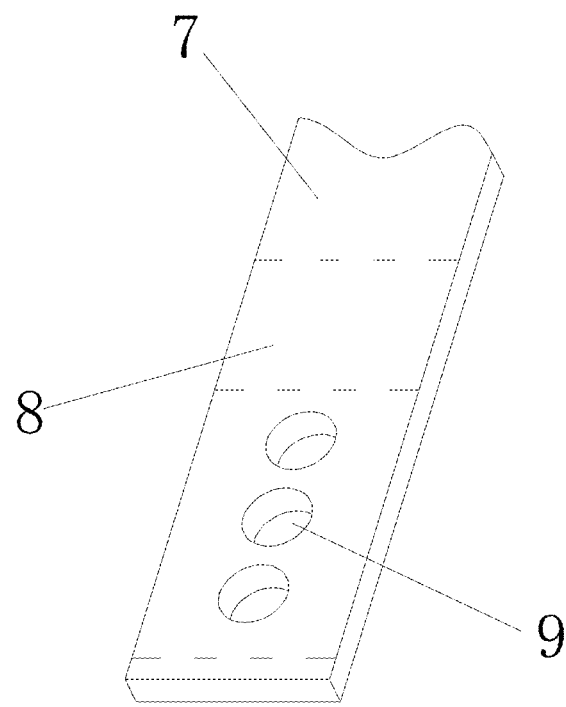
FIG. 2 is a schematic perspective view of an electrochemical electrode of the present invention.

Referring to FIGS. 1 and 2, an electrochemical electrode whose electrode matrix 1 is made of polymer film (PI) (illustrated by source or manufacturer), PI has a thickness of 20 μm to 200 μm, preferably a thickness of at least 20 μm; and both sides of electrode matrix 1 are deposited a gold layers 2 (the gold layer serves as an electrode, and any other metal can be used as a conductor) and 20 by the surface metallization technology, and the gold layers 2, 20 on both sides of the electrode matrix 1 has a thickness of at least 5 μm, and the two gold layers 2 and 20 serve as a working electrode A and a reference-counter electrode B respectively; the working electrode A is covered by a platinum black layer 3, a carbon nanotube/Nafion mesh layer 4, an enzyme biochemical sensitive layer 5, a polyurethane protection layer 6 respectively from the gold layer 2 to the outside; and the reference-counter electrode B is covered by a platinum black layer 30 and a polyurethane protection layer 60 respectively from gold layer 20 to outside. The electrode matrix 1 is provided with a through hole 9 that passes through the polyurethane protection layers 6 and 60 on both sides, and the through hole 9 is a circular hole, and the circular hole is coated with a hydrophilic polymer layer.

Surface metallization technology is a prior art. In recent years, bionics studies have shown that, dopamine can undergo oxidative polymerization under aqueous conditions, forming a strong adhesive composite layer on a series of solid materials such as polymers, metals, ceramics, glass, and woods, etc., while the catechol group of dopamine can exert a certain binding force on the metal, and the polydopamine composite layer has strong reducing ability to metal ions; when the modification materials deposited with a polydopamine layer on the surface are immersed in the metal salt solution, the composite layer reduces metal cations from the solution and deposits them on the surface of the material, to achieve the surface metallization of the electroless materials.

Example 1-2

Figure 3:
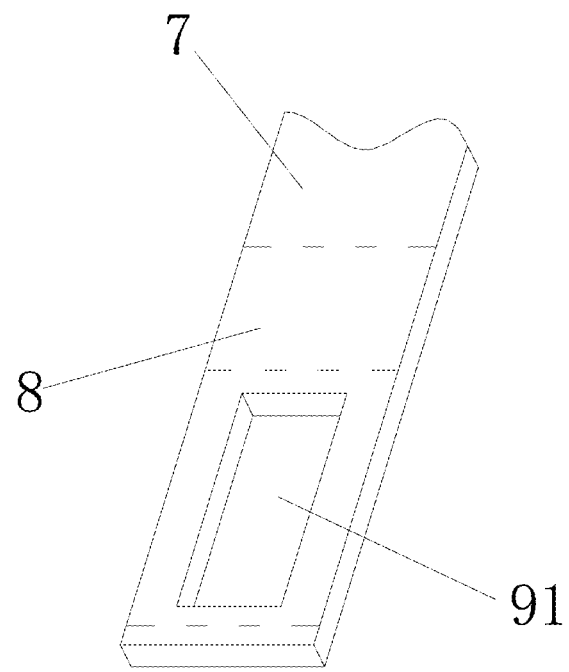
FIG. 3 is a schematic perspective structural view of an electrochemical electrode according to a second embodiment of the present invention.

On the basis of Example 1 and referring to FIG. 3, the electrode matrix 1 is provided with a square hole 91 passing through the polyurethane protective layers 6 and 60 on both sides, and the square hole 91 is coated with a hydrophilic polymer layer.

Example 1-3

Figure 4:
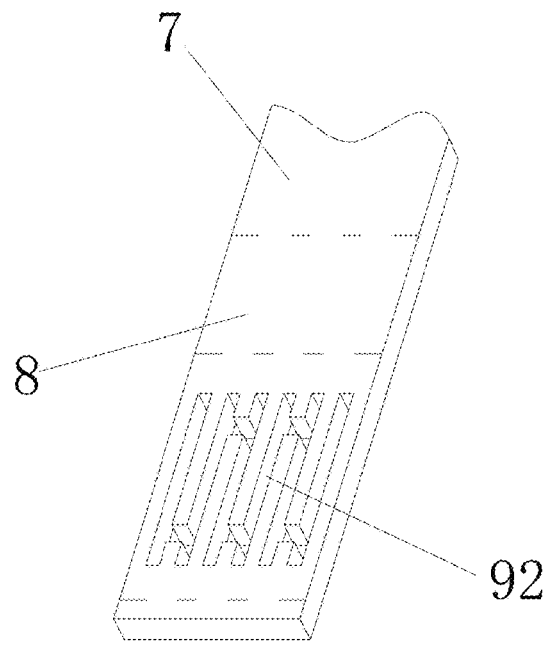
FIG. 4 is a schematic perspective structural view of an electrochemical electrode according to a second embodiment of the present invention.

On the basis of Example 1 and referring to FIG. 4, the electrode matrix 1 is provided with a through hole 92 passing through the polyurethane protective layers 6 and 60 on both sides. The through hole 92 has a cross section of interdigitated comb shape, and the through hole 92 is coated with a hydrophilic polymer layer.

Example 2

On the basis of Example 1, a continuous glucose monitoring sensor comprises a base and an electrochemical electrode described in the Example 1. The electrochemical electrode is disposed below the base, and the tip of the electrode is needle-shaped, and the electrode tail end is vertically fixed to the base. The needle-shaped electrode can be directly implanted into the subcutaneous tissues. As it is a single-sheet double-sided electrode structure, it has small implantation trauma; in addition, it effectively simplifies the processing technology and reduces the production cost. The base may be further provided with a wireless transmission device, which converts the monitoring data of the sensor into signals and outputs them to an external cloud data management module for storage. Through the cloud data management module, the data and values are monitored in a real-time manner. The cloud data management module may be a computer, a handset, a table PC, etc.

Example 3

Figure 5A:
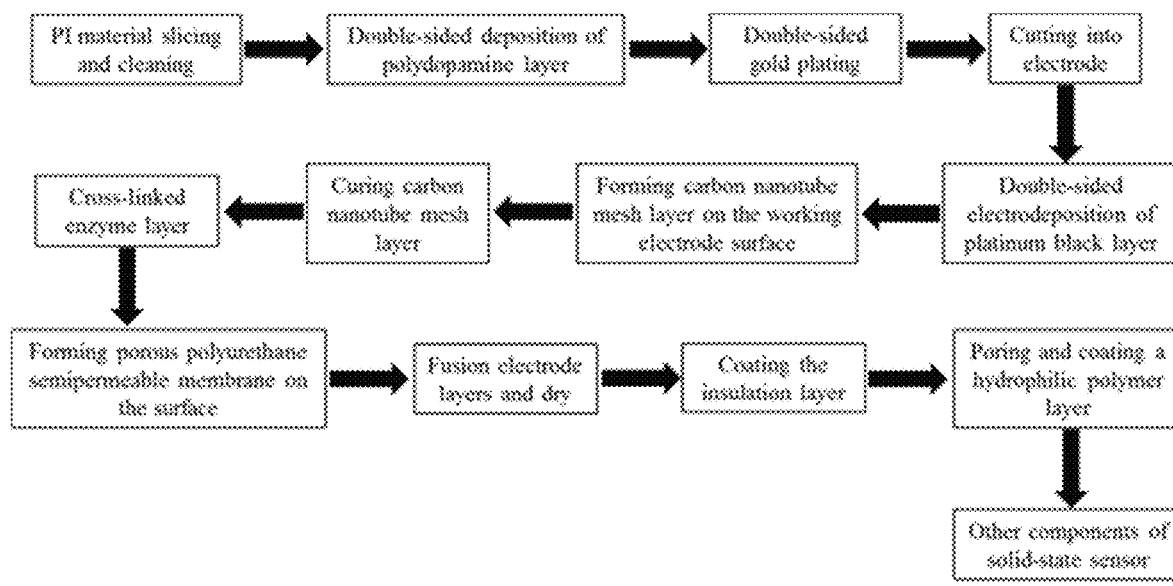
FIG. 5A is a flow chart of a process for preparing a continuous glucose monitoring sensor according to an embodiment of the present invention.
Figure 5B:
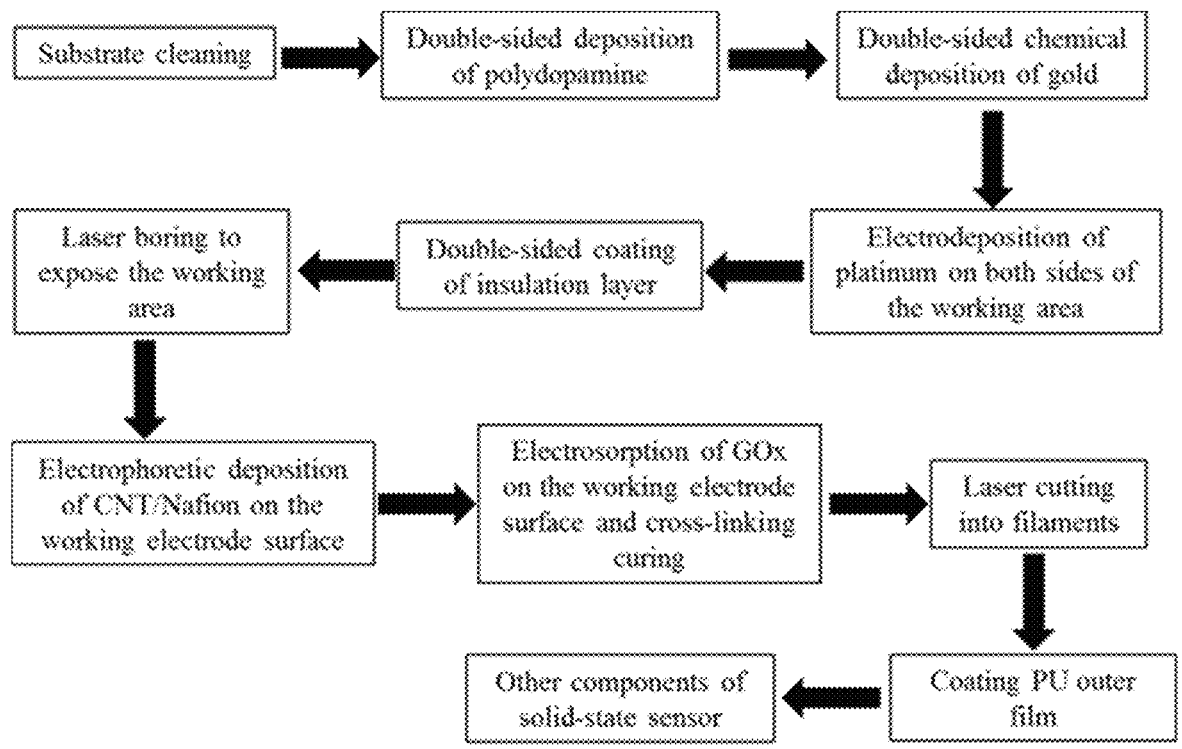
FIG. 5B is a flow chart of a process for preparing a continuous glucose monitoring sensor according to another embodiment of the present invention.

On the basis of Embodiments 1 and 2 and referring to FIG. 5, a method for preparing a continuous glucose monitoring sensor according to the embodiment 2, comprising the following steps:

① PI slice decontamination: cutting a polymer film material having a thickness of 120 μm into a sheet, and placing them in acetone, ethanol, deionized water for ultrasonic treatment for 5 min and drying, to remove the oil dirt on the surface;

② depositing polydopamine layer: immersing the cleaned sheet in a dopamine hydrochloride solution (pH 8.5, 2 mg/ml), placing it on a bleaching shaker at room temperature, and after oxidizing in air for 24 hours, a layer of polydopamine is formed on the surface of the sheet, after immersed and cleaned in deionized water for 8 hours, dried in a 80° C. oven ③ depositing catalytic layer: immersing the dried sheet in a 0.1 wt % Stearyl Trimethyl Ammonium Chloride (STAC) solution for 5 s, and taking out for drying, then placing it in platinum nanosol for 30 min, adsorbing a randomly distributed platinum nanoparticle layer on the surface of the sheet as a catalytic layer, and taking out, gently rinsing the surface with deionized water, to remove the unimmobilized platinum nanoparticles and dry;

The method of preparing platinum nanosol is as follows: dissolving 0.25 mmol of chloroplatinic acid in 91.5 ml of water, dissolving 5 mg of PVP in 5 ml of water and adding to the chloroplatinic acid solution, then dissolving 1 mmol of sodium borohydride in 10 ml of water, taking 1 ml and slowing adding to the mixed solution of PVP and chloroplatinic acid, after shaking vigorously, standing at room temperature for 24 hours.

④ chemically depositing gold layer: placing the dried sheet into a gold plating liquid (containing 10 mM chloroauric acid and 20 mM hydrogen peroxide) for 15 minutes, and then quickly placing in a 120° C. oven for annealing for 50 min, and turning off the oven, when the temperature in the oven has dropped to room temperature, taking out the sheet, at this time, a layer of bright, compact and firm gold is deposited on the surface of the sheet, with a thickness of about 10 μm;

⑤ Electrodepositing platinum layer: placing the cleaned gold-plated electrode on a platinum plating solution (3 wt % chloroplatinic acid, 0.25 wt % lead acetate), and setting the working potential at −2.5 V and the deposition time at 120 s by the constant-voltage method using platinum filament as a counter electrode; electrodepositing a compact platinum black layer on both sides of the electrode simultaneously, and sputtering or coating an insulating layer 8 on both sides of the sheet;

⑥ Parylene insulation treatment

Sputtering or coating a Parylene insulating layer on both sides of the sheet;

⑦ boring to form a working surface

Making a through hole (9) by laser on the surface of the set electrode working area to form a working area, and setting the pore size at 0.12 mm;

⑧ Adsorbing carbon nanotube mesh layer: immersing the electrode in aqueous dispersion liquid of carbon nanotube (carbon nanotube aqueous dispersion liquid: 5 wt % Nafion=1:4), setting a working voltage of 1 V and a working time of 10 s by the potentiostatic method, to form a carbon nanotube mesh layer on the outer peripheral surface of the working electrode hole.

⑨ crosslinking and curing: overhanging the electrode in a container with 25% glutaraldehyde at the bottom, crosslinked in a 40° C. oven for 60 min, and storing in a refrigerator at 4° C. for 2 h to firmly bond the carbon nanotube mesh layer with the substrate ⑩ Electro-absorbing $GO_X$ enzyme layer: dissolving a mixed powder of 300 mg of bovine serum albumin (BSA) and 1 g of glucose oxidase ($GO_X$) in 40 ml of deionized water to form a $GO_X$ enzyme solution, immersing the electrode in the $GO_X$ enzyme solution, setting the working voltage at 0.3V and the working time at 2400 s by the potentiostatic method using the side of the carbon nanotube mesh layer as the working electrode and the other side as the counter electrode, then electro-adsorbing $GO_X$ to the working electrode, then storing the electrode in a 4° C. refrigerator for 8 h, so that $GO_X$ is fully embedded in the carbon nanotube mesh layer, finally, after cross-linking for 40 min with the cross-linking and curing method described in step ⑨, storing the mixture in a 4° C. refrigerator for 8 h, so that the enzyme layer is fully crosslinked and cured, and then rinsing off the insufficiently immobilized enzyme with deionized water;

⑪ Cutting electrode: cutting the sheet into a filament-like, single-layer double-sided electrode using an ultraviolet laser cutting machine, and setting the size of the implanted part at 0.25 mm×5 mm;

⑫ Forming a polyurethane protection layer: dissolving 4 wt % of polyurethane in a mixed solution of 98 v % tetrahydrofuran and 2 v % dimethylformamide to form a polyurethane solution, slowly passing the electrode sensing portion through a steel wire ring with an inner diameter of 2 mm soaked with the polyurethane solution, to form a polyurethane protection layer on the surface of the electrode;

⑬ Assembling an electrode: fixing the electrode tail end to the base, and the lead wire area (7) on the electrode tail end is electrically connected to the sensing component in the base.

The electrode prepared in the above steps ① to ⑬ can be placed in a drying oven at 25° C. for future use if it needs to be stored.

For the sensor electrode prepared by the method, the gold layer is tightly bound with the surface of the PI, and the gold nanoparticles are neat, compact and evenly distributed. The gold layer has high uniformity and compactness, and compared with the gold layer formed by other processing technologies, the gold layer can be subjected to the electrochemical deposition of platinum and other functional modifications on its surface, without producing peel-off or falling off of the metal layer and the non-metal layer over the deposition time (explained or demonstrated by experimental data?) Furthermore, as the electrode working surface is a gold/platinum layer having a thickness of about 10-15 μm at the edge of a circular hole, the micron-scale electrode structure effectively enhances the mass transfer performance and enhances the electrochemical reaction performance. The combined through hole structure and carbon nanotube porous structure has the effect of increasing the enzyme loading capacity and protecting the enzyme activity, and enhancing the long-term stability of the sensor (explained or demonstrated by experimental data?)

Figure 6:
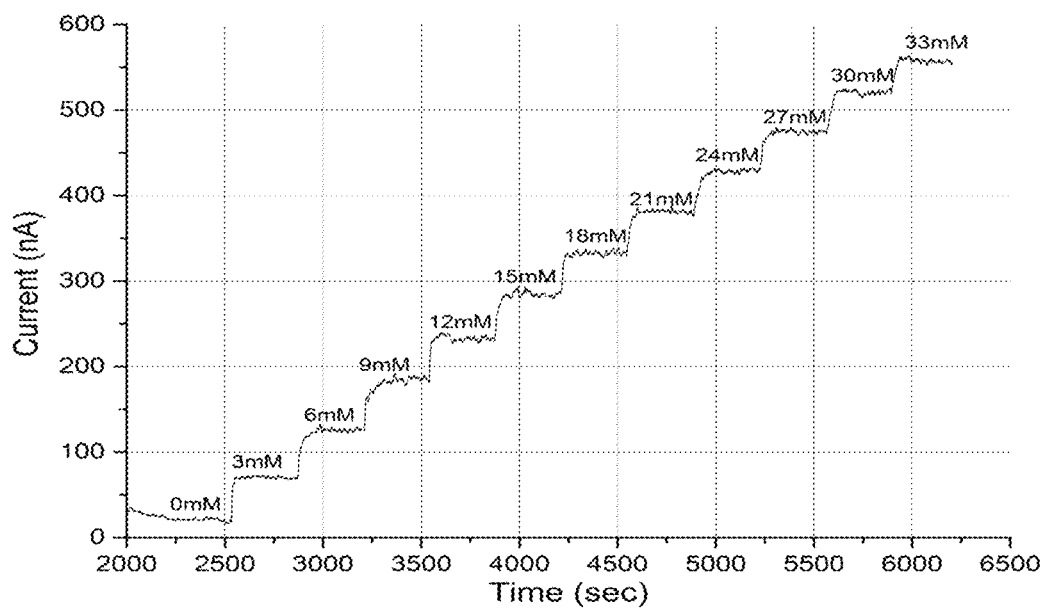
FIG. 6 is a data analysis graph of glucose monitoring performance test of the sensor of the present invention.
Figure 7:
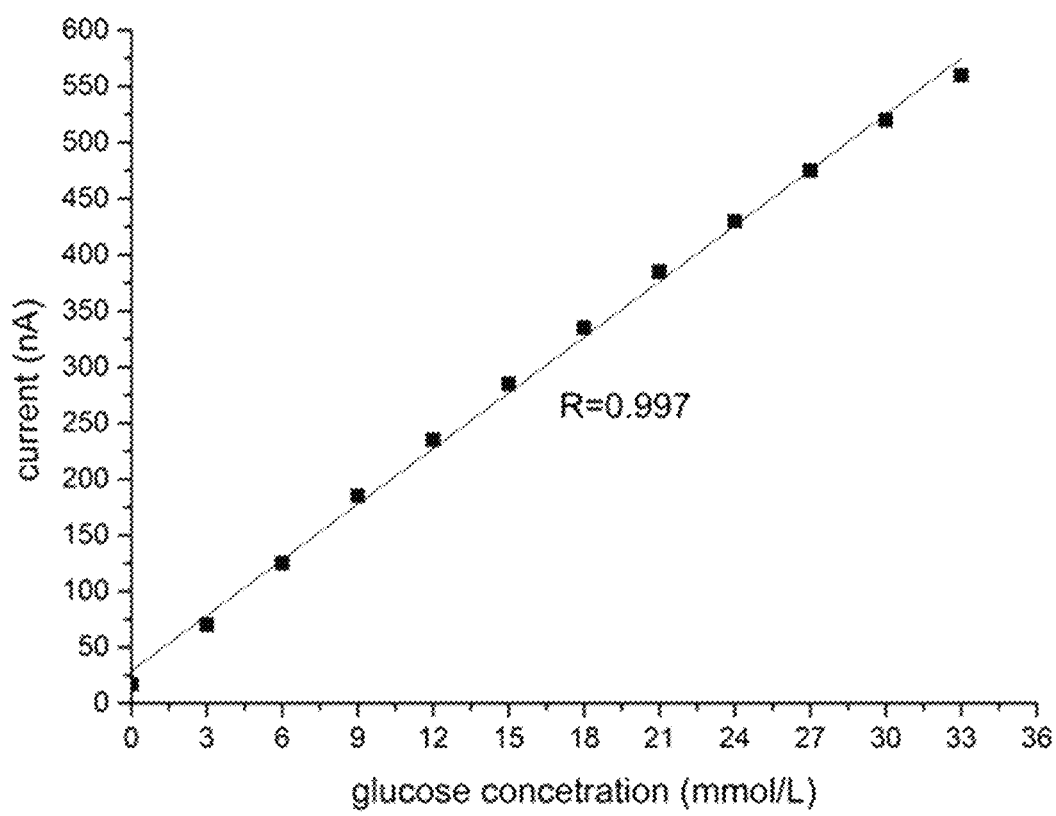
FIG. 7 is a data analysis graph of anti-interference test of uric acid, ascorbic acid and ibuprofen of the sensor of the present invention.
Figure 8:
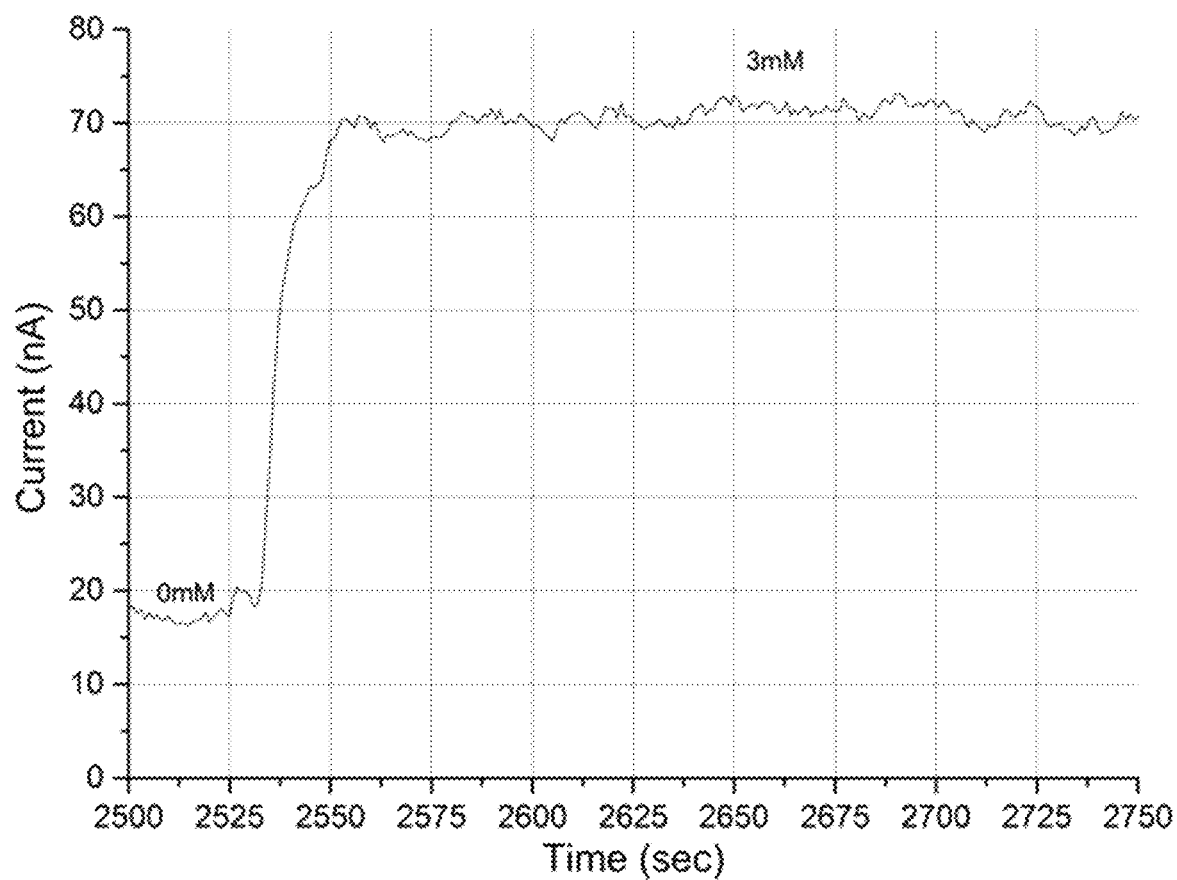
FIG. 8 shows a response change process of the sensor prepared according to the embodiments of the present invention from 0 mM to 3 mM.

Glucose continuous response test: Inject 10 ml of blank PBS solution (pH 7.2) into the detection cell, place the detection cell on the magnetic stirrer platform, to keep the heating surface of the magnetic stirrer at (37° C.±2° C.) for at least 5 min, and maintain the detection cell temperature at 37° C.±2° C. and the magnet speed at 200 rpm. Immerse the sensor 5 mm below the surface of the solution in the detection chamber and conduct a continuous response test using a chronoamperometry (i-t). The constant voltage potential is set at 0.3V. After power-on and initialization for more than 40 min, inject a certain amount of glucose solution to the detection cell, so that the glucose concentration in the detection cell continuously rises from 0 to 33 mM, as shown in FIG. 6. FIG. 7 shows the linearity of the sensor, and FIG. 8 shows the response change process from 0 mM to 3 mM. As shown from the figures, the sensor has a wide linear response range, and its linearity is over 99% and sensitivity is up to 100 μAcm−2(mmol/L)−1 in the range of 0~30 mM. The sensor also has a fast response speed. Considering the effect of each injection of glucose on the concentration equilibrium time of the detection cell, the response time of each gradient concentration change is within the range of 15~30 s and the average response time is about 25 s.

Figure 9:
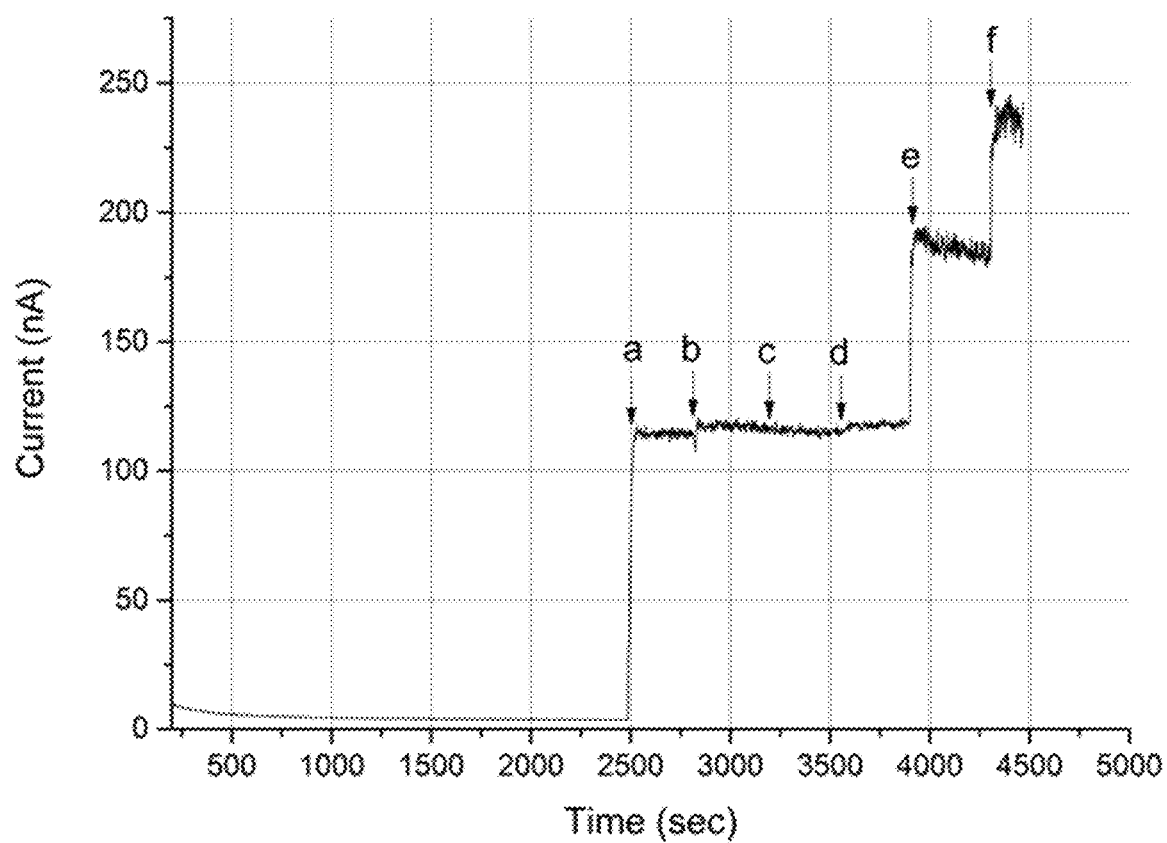
FIG. 9 shows a data analysis chart of anti-interference tests of ascorbic acid, uric acid and acetaminophen on the sensor.

FIG. 9 shows the data analysis chart of anti-interference tests of ascorbic acid, uric acid and acetaminophen on the sensor, wherein, a. 4.0 mmol/L glucose; b. 0.1 mmol/L ascorbic acid; c. 0.5 mmol/L uric acid d. 0.2 mmol/L acetaminophen; e. 4.0 mmol/L glucose; f. 4.0 mmol/L glucose. As shown from the figure, the glucose monitoring sensor in the present invention has good anti-interference to uric acid, ascorbic acid and acetaminophen, and it has a porous inner layer of Nafion/carbon nanotube network, playing a positive role for the anti-interference of the sensor. In addition, the sensor structure has a close gap between the working electrode and the reference-counter electrode, so that the sensor can still exhibit a better detection range and linear range at an operating voltage below 0.5V.

For the glucose monitoring sensor in the present invention, the enzyme layer is dissolved in a porous network structure formed by the Nafion/carbon nanotubes, which greatly increases the enzyme load, reduces the opportunity for glucose molecules to enter the electrode layer directly and effectively promotes the stability of the response current.

All patents and publications mentioned in the specification of the present invention are disclosed art and can be used in the present invention. All patents and publications cited herein are incorporated by reference as they are cited as reference separately. The invention described herein can be achieved in the absence of any element or elements, a limitation or limitations, and such limitations are not specifically described herein. For example, the terms "comprising", "essentially consisting of" and "consisting of" in each of the examples herein may be replaced with the remaining two terms of either. The terms and expressions used herein are illustrative rather than limitation, and they are not intended to exclude any equivalent features of these terms and expressions described herein, however, it should be aware that any appropriate changes or modifications within the scope of the invention and claims may be made. It should be understood that the embodiments of the present invention are described in the preferred embodiments of the present invention, and that various modifications and changes can be made by those skilled in the art in accordance with the teachings of the present invention. These modifications and changes should be considered to fall into the scope of the invention and the scope of the independent claims and the appended claims.

The invention claimed is:

1. A method of making a sensor, comprising the following steps:
   preparing an electrochemical electrode comprising the following steps:
      providing an electrode substrate made of a polymer film;
      forming a first gold layer as a working electrode on one surface of the electrode substrate;
      forming a second gold layer as a reference-counter electrode on another surface of the electrode substrate;
      forming a first platinum black layer on the working electrode, forming a carbon nanotube mesh layer on the first platinum black layer, forming an enzyme biochemical sensitive layer on the carbon nanotube mesh layer, and forming a first polyurethane protection layer on the enzyme biochemical sensitive layer; and forming a second platinum black layer on the reference-counter electrode, and forming a second polyurethane protection layer on the second platinum black layer; and fixing the electrochemical electrode to a base, and electrically connecting the electrochemical electrode to a sensing component in the base, wherein the electrode substrate is subjected to decontamination, which comprises the following steps: cutting a polymer film material having a thickness of at least 20 μm into a sheet as the electrode substrate, placing the electrode substrate in an organic solvent, the organic solvent being acetone or ethanol; and performing ultrasonic treatment in deionized water for 5 minutes on the electrode substrate and drying the electrode substrate, and then removing oil dirt on surfaces of the electrode substrate;

wherein after decontamination, depositing polydopamine layers on the surfaces of the electrode substrate comprises the following steps: immersing the cleaned electrode substrate in a dopamine hydrochloride solution with a concentration of 2 mg/ml at pH 8.5, placing the electrode substrate on a bleaching shaker at room temperature, after oxidizing the electrode substrate in air for 24 hours, layers of polydopamine being formed on the surfaces of the electrode substrate, and after immersing and cleaning the electrode substrate in deionized water for 8 hours, drying the electrode substrate in an oven at 80° C.;

wherein after depositing polydopamine layers on the surfaces of the electrode substrate, depositing catalytic layers on the surfaces of the electrode substrate comprises the following steps: immersing the dried electrode substrate in a 0.1 wt % stearyl trimethyl ammonium chloride (STAC) solution for 5 s, and taking out the electrode substrate for drying, then placing the electrode substrate in platinum nanosol for 30 min, adsorbing platinum nanoparticle layers on the surfaces of the electrode substrate, and taking out the electrode substrate, gently rinsing the surfaces with deionized water to remove unimmobilized platinum nanoparticles and drying the electrode substrate.

2. A method of making a sensor, comprising the following steps:

preparing an electrochemical electrode comprising the following steps:

providing an electrode substrate made of a polymer film;

forming a first gold layer as a working electrode on one surface of the electrode substrate;

forming a second gold layer as a reference-counter electrode on another surface of the electrode substrate;

forming a first platinum black layer on the working electrode, forming a carbon nanotube mesh layer on the first platinum black layer, forming an enzyme biochemical sensitive layer on the carbon nanotube mesh layer, and forming a first polyurethane protection layer on the enzyme biochemical sensitive layer; and forming a second platinum black layer on the reference-counter electrode, and forming a second polyurethane protection layer on the second platinum black layer; and fixing the electrochemical electrode to a base, and electrically connecting the electrochemical electrode to a sensing component in the base;

wherein the electrode substrate is subjected to decontamination, which comprises the following steps: cutting a polymer film material having a thickness of at least 20 μm into a sheet as the electrode substrate, placing the electrode substrate in an organic solvent, the organic solvent being acetone or ethanol; and performing ultrasonic treatment in deionized water for 5 minutes on the electrode substrate and drying the electrode substrate, and then removing oil dirt on surfaces of the electrode substrate;

wherein the step of forming the first gold layer as the working electrode on one surface of the electrode substrate and forming the second gold layer as the reference-counter electrode on another surface of the electrode substrate comprises the following steps: placing the dried electrode substrate into a gold plating liquid containing 10 mM chloroauric acid and 20 mM hydrogen peroxide for 15 minutes, then placing the electrode substrate in an oven at 120° C. for annealing for 50 min, turning off the oven, and when the temperature in the oven has dropped to the room temperature, taking out the electrode substrate, wherein at this time, layers of bright, compact and firm gold are deposited on the surfaces of the electrode substrate to obtain a cleaned gold-plated electrode;

wherein the step of forming the first platinum black layer on the working electrode and forming the second platinum black layer on the reference-counter electrode comprises the following step: placing the cleaned gold-plated electrode in a platinum plating solution consisting of 3 wt % chloroplatinic acid and 0.25 wt % lead acetate, and setting a working potential at −2.5 V and a deposition time at 120 s by a constant-voltage method using a platinum filament as a counter electrode; and electrodepositing compact platinum black layers on both sides of the cleaned gold-plated electrode simultaneously;

wherein forming the carbon nanotube mesh layer on the first platinum black layer comprises the following steps: immersing the cleaned gold-plated electrode with the first and second platinum black layers in an aqueous dispersion liquid of carbon nanotube with carbon nanotube aqueous dispersion liquid: 5 wt % Nafion=1:4 in volume, setting a working voltage of 1 V and a working time of 10 s by a potentiostatic method, and forming the carbon nanotube mesh layer on the first platinum black layer.

3. The method according to claim 2, further comprising:

parylene insulation treatment: sputtering or coating a parylene insulating layer on both sides of the gold-plated electrode with the first and second platinum black layers;

boring to form a working area: making a through hole on the gold-plated electrode with the first and second platinum black layers by laser, and an area where the through hole is located being the working area for the electrochemical electrode;

crosslinking and curing: overhanging the gold-plated electrode with the first and second platinum black layers and the carbon nanotube mesh layer in a container with 25% glutaraldehyde at a bottom of the container, placing the gold-plated electrode with the first and second platinum black layers and the carbon nanotube mesh layer in the container in an oven at 40° C. for 60 min for cross-linking, and storing the gold-plated electrode with the first and second platinum black layers and the carbon nanotube mesh layer in the container in a refrigerator at 4° C. for 2 h to firmly bond the carbon nanotube mesh layer onto the first platinum black layer;

electro-adsorbing a glucose oxidase ($GO_X$): immersing a working part of the gold-plated electrode with the first and second platinum black layers and the carbon nanotube mesh layer in a $GO_X$ enzyme solution with bovine serum albumin (BSA): $GO_X$=1:3 in weight at a concentration of 30 mg/ml, setting a working voltage at 0.3 V and a working time at 2400 s by a potentiostatic method, then storing the gold-plated electrode with the first and second platinum black layers and the carbon nanotube mesh layer in a refrigerator at 4° C. for 8 h, so that $GO_X$ is fully embedded in the carbon nanotube mesh layer to form the $GO_X$ enzyme layer;

cutting the electrode obtained in the step of electro-adsorbing the $GO_X$ enzyme layer: cutting the electrode obtained in the step of electro-adsorbing the $GO_X$ enzyme layer into a filament, single-layer double-sided electrode using an ultraviolet laser cutting machine;

forming the first and second polyurethane protection layers: dissolving 4 wt % of polyurethane in a mixed solution of 98 v % tetrahydrofuran and 2 v % dimethylformamide to form a polyurethane solution, slowly passing a sensing portion of the filament, single-layer double-sided electrode through a steel wire ring with an inner diameter of 2 mm soaked with the polyurethane solution, to form the first and second polyurethane protection layers on the surfaces of the filament, single-layer double-sided electrode to obtain the electrochemical electrode;

assembling the electrochemical electrode: fixing a tail end of the electrochemical electrode to the base, and electrically connecting a lead wire area on the tail end to the sensing component in the base.

4. A method of making a sensor, comprising the following steps:

cutting and decontamination: cutting a polymer film material having a thickness of at least 20 μm into a sheet as an electrode substrate, and placing the electrode substrate in acetone, ethanol, deionized water for ultrasonic treatment for 5 min and drying the electrode substrate to remove oil dirt on surfaces of the electrode substrate;

depositing polydopamine layers: immersing the cleaned electrode substrate in a dopamine hydrochloride solution with a concentration of 2 mg/ml at pH 8.5, placing the electrode substrate on a bleaching shaker at room temperature, after oxidizing the electrode substrate in air for 24 hours, layers of polydopamine being formed on the surfaces of the electrode substrate, and after immersing and cleaning the electrode substrate in deionized water for 8 hours, drying the electrode substrate in an oven at 80° C.;

depositing catalytic layers: immersing the dried electrode substrate in a 0.1 wt % stearyl trimethyl ammonium chloride (STAC) solution for 5 s, and taking out the electrode substrate for drying, then placing the electrode substrate in platinum nanosol for 30 min, adsorbing platinum nanoparticle layers on the surfaces of the electrode substrate, and taking out the electrode substrate, gently rinsing the surfaces with deionized water to remove unimmobilized platinum nanoparticles and drying the electrode substrate;

chemically depositing gold layers: placing the dried electrode substrate into a gold plating liquid containing 10 mM chloroauric acid and 20 mM hydrogen peroxide for 15 minutes, then placing the electrode substrate in an oven at 120° C. for annealing for 50 min, turning off the oven, and when the temperature in the oven has dropped to the room temperature, taking out the electrode substrate, wherein at this time, layers of bright, compact and firm gold are deposited on the surfaces of the electrode substrate to obtain a cleaned gold-plated electrode;

electrodepositing platinum black layers: placing the cleaned gold-plated electrode in a platinum plating solution consisting of 3 wt % chloroplatinic acid and 0.25 wt % lead acetate, and setting a working potential at −2.5 V and a deposition time at 120 s by a constant-voltage method using a platinum filament as a counter electrode; and electrodepositing compact platinum black layers on both sides of the cleaned gold-plated electrode simultaneously;

parylene insulation treatment:

sputtering or coating parylene insulating layers on both sides of the gold-plated electrode with the platinum black layers;

boring to form a working area: making a through hole by laser on the gold-plated electrode with the platinum black layers, and an area where the through hole is located being the working area for the electrochemical electrode;

adsorbing to form a carbon nanotube mesh layer: immersing the gold-plated electrode with the platinum black layers in an aqueous dispersion liquid of carbon nanotube with carbon nanotube aqueous dispersion liquid: 5 wt % Nafion=1:4 in volume, setting a working voltage of 1 V and a working time of 10 s by a potentiostatic method, and forming the carbon nanotube mesh layer on an outer surface of the gold-plated electrode with the platinum black layers;

crosslinking and curing: overhanging the gold-plated electrode with the platinum black layers and the carbon nanotube mesh layer in a container with 25% glutaraldehyde at a bottom of the container, placing the gold-plated electrode with the platinum black layers and the carbon nanotube mesh layer in the container in an oven at 40° C. for 60 min for cross-linking, and storing the gold-plated electrode with the platinum black layers and the carbon nanotube mesh layer in the container in a refrigerator at 4° C. for 2 h to firmly bond the carbon nanotube mesh layer with the gold-plated electrode with the platinum black layers;

electro-absorbing a $GO_X$ enzyme layer: immersing a working part of the gold-plated electrode with the first and second platinum black layers and the carbon nanotube mesh layer in a $GO_X$ enzyme solution with BSA: $GO_X$=1:3 in weight at a concentration of 30 mg/ml, setting a working voltage at 0.3 V and a working time at 2400 s by a potentiostatic method, then storing the gold-plated electrode with the first and second platinum black layers and the carbon nanotube mesh layer in a refrigerator at 4° C. for 8 h, so that $GO_X$ is fully embedded in the carbon nanotube mesh layer to form the $GO_X$ enzyme layer;

cutting the electrode obtained in the step of electro-adsorbing the $GO_X$ enzyme layer: cutting the electrode obtained in the step of electro-adsorbing the $GO_X$ enzyme layer into a filament, single-layer double-sided electrode using an ultraviolet laser cutting machine;

forming polyurethane protection layers: dissolving 4 wt % of polyurethane in a mixed solution of 98 v % tetrahydrofuran and 2 v % dimethylformamide to form a polyurethane solution, slowly passing a sensing portion of the filament, single-layer double-sided electrode through a steel wire ring with an inner diameter of 2 mm soaked with the polyurethane solution, to form polyurethane protection layers on the surfaces of the filament, single-layer double-sided electrode to obtain an electrochemical electrode;

assembling the electrochemical electrode: fixing a tail end of the electrode to a base, and electrically connecting a lead wire area on the tail end to a sensing component in the base.

5. The method according to claim 4, wherein the method of preparing the platinum nanosol comprises the following steps: dissolving 0.25 mmol of chloroplatinic acid in 91.5 ml of water to obtain a chloroplatinic acid solution, dissolving 5 mg of polyvinylpyrrolidone (PVP) in 5 ml of water and adding the 5 mg of PVP dissolved in the 5 ml of water to the chloroplatinic acid solution, then dissolving 1 mmol of sodium borohydride in 10 ml of water, taking 1 ml of the 1 mmol of sodium borohydride dissolved in the 10 ml of water and slowing adding the 1 ml of the 1 mmol of sodium borohydride dissolved in the 10 ml of water to the mixed solution of PVP and chloroplatinic acid, after shaking the mixed solution vigorously, keeping the mixed solution at room temperature for 24 hours.

\* \* \* \* \*